(12) United States Patent
Butler et al.

(10) Patent No.: US 11,730,529 B2
(45) Date of Patent: Aug. 22, 2023

(54) POWERED MODULAR HEAD LOCKER

(71) Applicant: Warsaw Orthopedic, Inc., Warsaw, IN (US)

(72) Inventors: Brian A. Butler, Atoka, TN (US); Aubrey R. Mills, Memphis, TN (US); Christel Italiaie, Memphis, TN (US); Bret M. Wilfong, Hernando, MS (US); Madeline G. Wilson, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 661 days.

(21) Appl. No.: 16/830,377

(22) Filed: Mar. 26, 2020

(65) Prior Publication Data

US 2021/0298810 A1    Sep. 30, 2021

(51) Int. Cl.
*A61B 17/88* (2006.01)
*A61B 17/70* (2006.01)
*A61B 17/56* (2006.01)
*B25D 11/00* (2006.01)
*B25D 11/10* (2006.01)

(52) U.S. Cl.
CPC ...... *A61B 17/8875* (2013.01); *A61B 17/7082* (2013.01); *A61B 17/8886* (2013.01); *A61B 2017/564* (2013.01); *B25D 11/005* (2013.01); *B25D 11/102* (2013.01); *B25D 11/106* (2013.01)

(58) Field of Classification Search
CPC .............. A61B 17/8875; A61B 17/888; A61B 17/8886; A61B 17/8891; A61B 17/7082; A61B 2017/564; B25D 11/00; B25D 11/005; B25D 11/10; B25D 11/102; B25D 11/106
USPC ........................................................ 606/104
See application file for complete search history.

(56) References Cited

U.S. PATENT DOCUMENTS

| | | | |
|---|---|---|---|
| 4,098,351 A | * | 7/1978 | Alessio ................ B25D 11/005 74/56 |
| 7,988,699 B2 | | 8/2011 | Martz et al. |
| 8,221,431 B2 | | 7/2012 | Chenaux |
| 8,475,466 B2 | | 7/2013 | Chenaux |
| 8,757,035 B2 | | 6/2014 | Kerboul et al. |
| 8,806,973 B2 | | 8/2014 | Ross et al. |
| 8,900,280 B2 | | 12/2014 | Paroth et al. |
| 8,968,276 B2 | | 3/2015 | Zemlok et al. |
| 9,017,333 B2 | | 4/2015 | Beale et al. |
| 9,055,943 B2 | | 6/2015 | Zemlok et al. |
| 9,149,307 B2 | | 10/2015 | Sandstrom et al. |
| 9,446,507 B2 | | 9/2016 | Nino et al. |

(Continued)

*Primary Examiner* — Marcela I. Shirsat
(74) *Attorney, Agent, or Firm* — Fox Rothschild LLP

(57) ABSTRACT

Systems, instruments, and methods for operating a surgical instrument. The methods comprising: receiving at least a portion of an external object in a recess of a hollow shank; rotating a first shaft disposed within the hollow shank; using rotation of the first shaft to cause translational movement of a second shaft of the surgical instrument in a first direction away from the first shaft and along a central axis of the surgical instrument; applying a pushing force on the external object using the second shaft that is experiencing the translational movement; and causing translational movement of the second shaft in a second direction opposed from the first direction after the pushing force has been applied to the external object.

18 Claims, 9 Drawing Sheets

(56) References Cited

U.S. PATENT DOCUMENTS

| | | |
|---|---|---|
| 9,724,149 B2 | 8/2017 | Trieu et al. |
| 9,808,354 B2 | 11/2017 | Willis et al. |
| 9,820,740 B2 | 11/2017 | Zemlok et al. |
| 9,855,087 B2 | 1/2018 | Divincenzo et al. |
| 9,987,066 B2 | 6/2018 | Stad et al. |
| 10,045,787 B2 | 8/2018 | Krebs et al. |
| 10,076,374 B2 | 9/2018 | Diduch et al. |
| 10,160,105 B2 | 12/2018 | Nino et al. |
| 10,219,854 B2 | 3/2019 | Nino et al. |
| 10,274,021 B2 | 4/2019 | Victor et al. |
| 10,363,073 B2 | 7/2019 | Raina et al. |
| 10,433,883 B2 | 10/2019 | DiVincenzo et al. |
| 10,433,982 B2 | 10/2019 | Willis et al. |
| 10,478,235 B2 | 11/2019 | Beale et al. |
| 10,568,677 B2 | 2/2020 | DiVincenzo et al. |
| 10,582,925 B2 | 3/2020 | Marks et al. |
| 10,603,078 B2 | 3/2020 | Simpson et al. |
| 10,660,687 B2 | 5/2020 | Goodwin, Jr. et al. |
| 10,682,167 B2 | 6/2020 | Sandstrom et al. |
| 10,709,488 B2 | 7/2020 | Diduch et al. |
| 10,729,419 B2 | 8/2020 | Diduch et al. |
| 10,751,092 B2 | 8/2020 | Biedermann et al. |
| 10,765,466 B2 | 9/2020 | Stad et al. |
| 10,779,872 B2 | 9/2020 | Smith et al. |
| 10,869,751 B2 | 12/2020 | Diduch et al. |
| 10,874,448 B2 | 12/2020 | Rees et al. |
| 2007/0010816 A1 | 1/2007 | Wilkinson et al. |
| 2010/0249798 A1 | 9/2010 | Sournac et al. |
| 2011/0160775 A1 | 6/2011 | Carls et al. |
| 2012/0239095 A1 | 9/2012 | Barrall |
| 2018/0070941 A1 | 3/2018 | Zemlok et al. |
| 2019/0329388 A1 | 10/2019 | Erickson et al. |
| 2020/0030015 A1 | 1/2020 | Grizzard et al. |
| 2020/0100817 A1 | 4/2020 | DiVincenzo et al. |
| 2020/0100824 A1 | 4/2020 | DiVincenzo et al. |
| 2020/0113603 A1 | 4/2020 | Simpson et al. |
| 2020/0205805 A1 | 7/2020 | Marks et al. |
| 2020/0340558 A1 | 10/2020 | Riemhofer et al. |
| 2020/0375638 A1 | 12/2020 | Avidano et al. |
| 2020/0390478 A1 | 12/2020 | Rodriguez et al. |
| 2020/0390486 A1 | 12/2020 | Rodriguez et al. |

\* cited by examiner

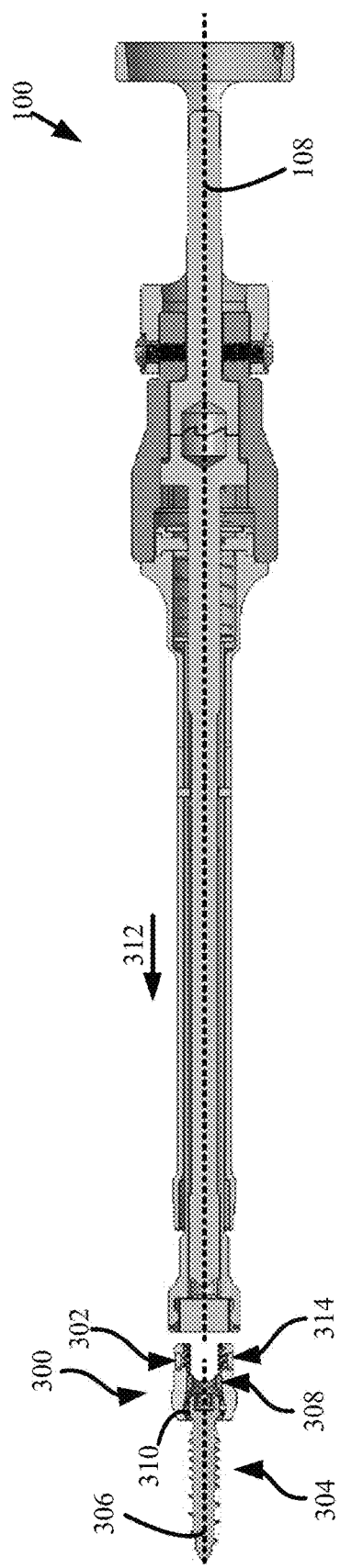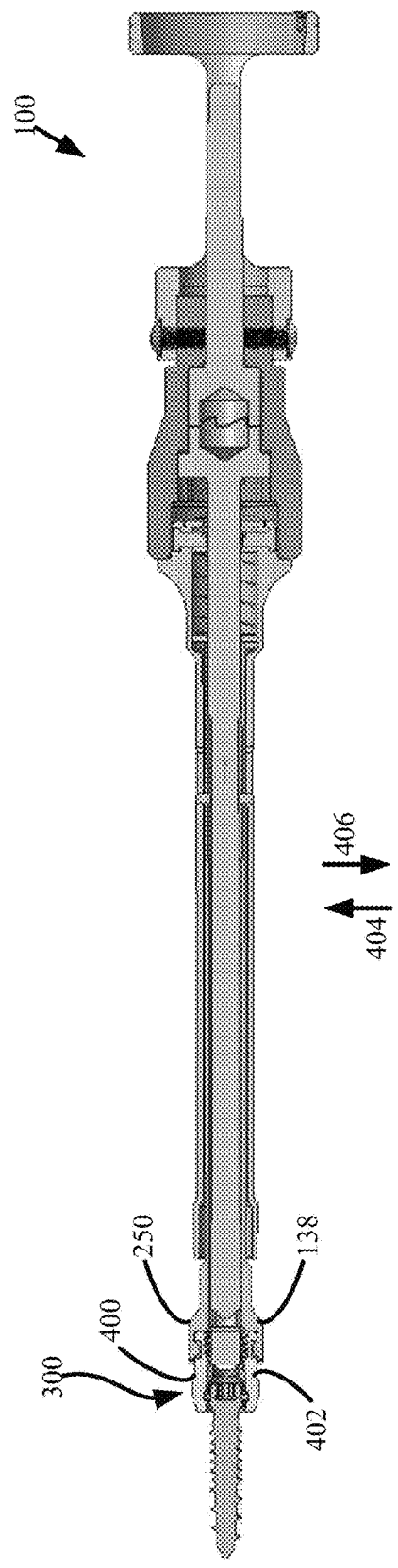
FIG. 3
FIG. 4

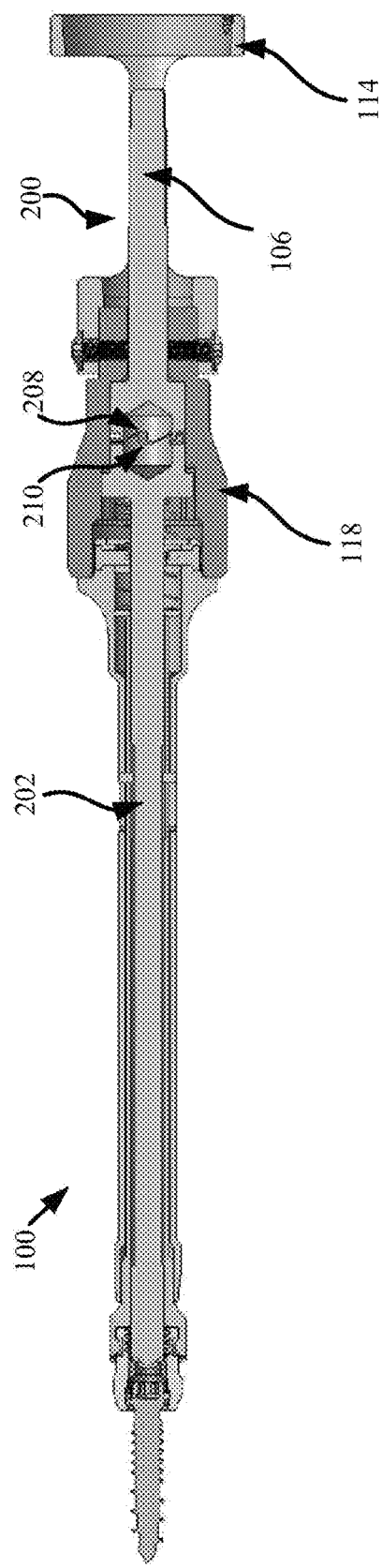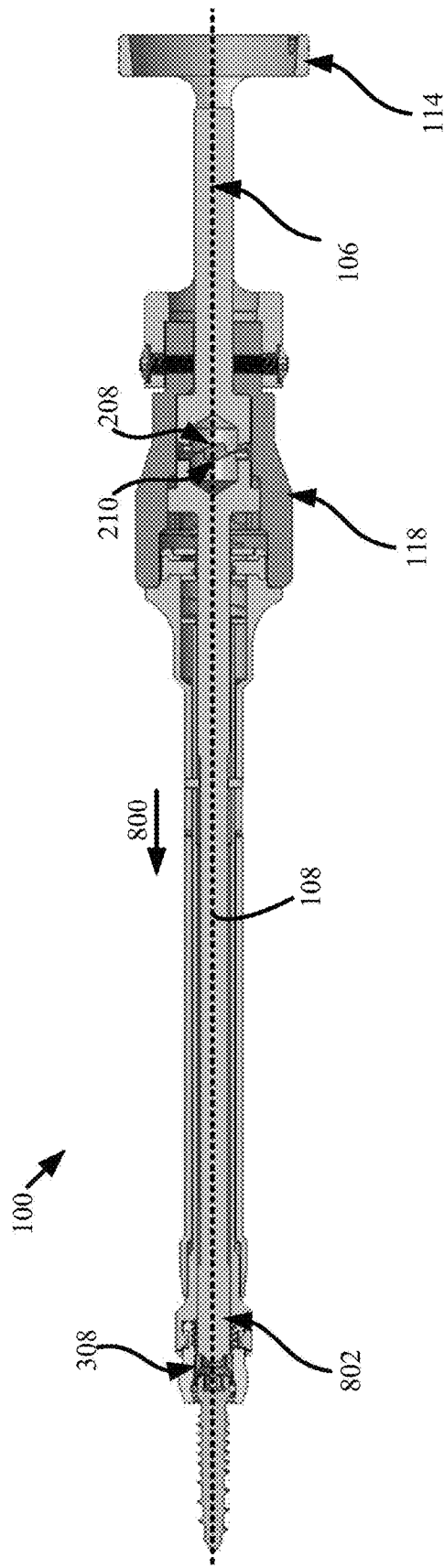
FIG. 7
FIG. 8

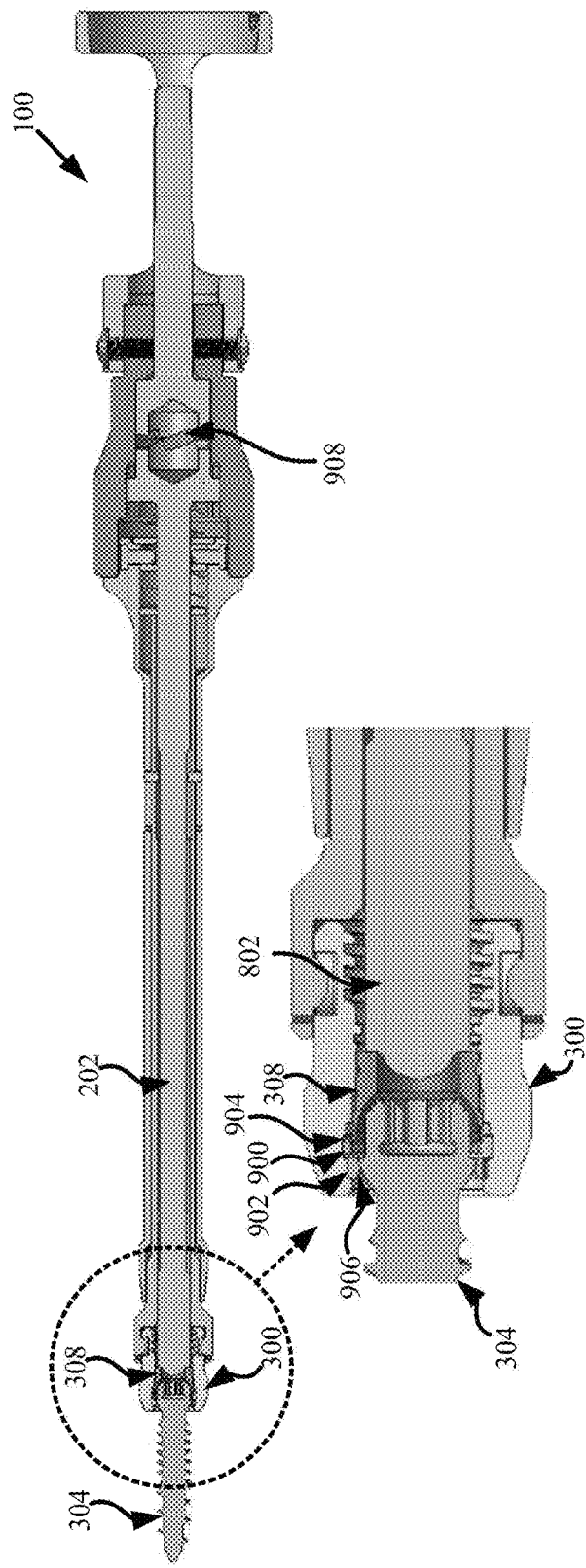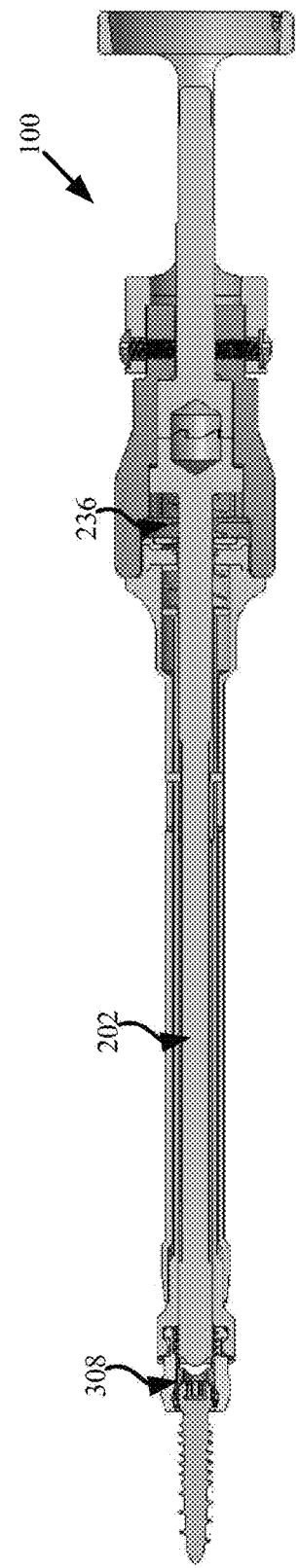
FIG. 9
FIG. 10

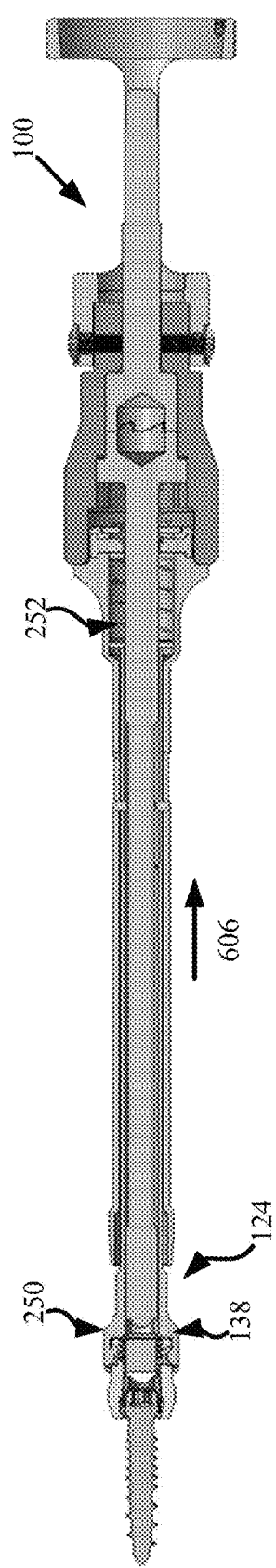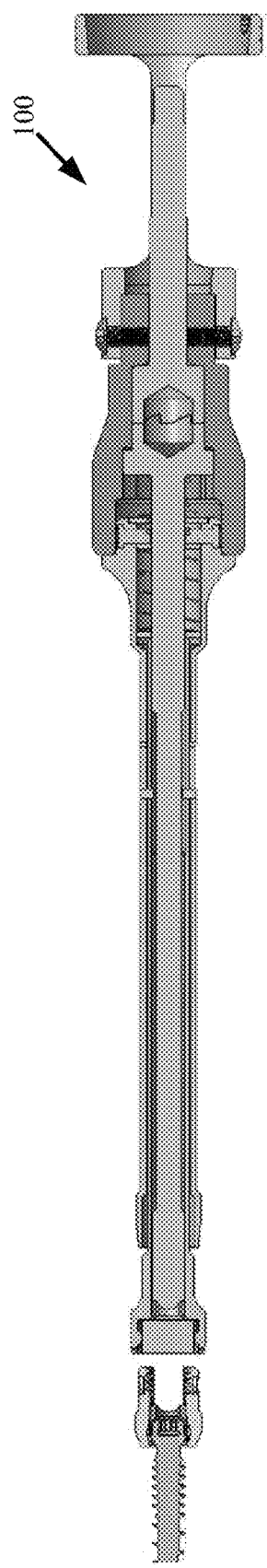
FIG. 11
FIG. 12

POWERED MODULAR HEAD LOCKER

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation, and exercise can be effective, however, may fail to relieve the symptoms associated with these disorders. Surgical treatment of these spinal disorders includes correction, fusion, fixation, discectomy, laminectomy, and/or implantable prosthetics. As part of these surgical treatments, spinal constructs, which include implants such as bone fasteners, connectors, plates, and vertebral rods are often used to provide stability to a treated region. These implants can redirect stresses away from a damaged or defective region while healing takes place to restore proper alignment and generally support the vertebral members. Surgical instruments are employed, for example, to engage the fasteners for attachment to two or more vertebral members. This disclosure describes improvements over these prior technologies.

SUMMARY

The present disclosure relates to implementing systems and methods for operating a surgical instrument. The methods may include: receiving at least a portion of an external object in a recess of a hollow shank; rotating a first shaft disposed within the hollow shank; using rotation of the first shaft to cause translational movement of a second shaft along a central axis of the surgical instrument in a first direction towards the recess; applying a pushing force on the external object using the second shaft that is experiencing the translational movement; and causing translational movement of the second shaft in a second direction opposed from the first direction after the pushing force has been applied to the external object. The translational movement of the second shaft part in each of the first and second directions may be caused by (i) a sliding engagement between ramped surfaces of the first and second shaft parts and/or (ii) a resilient member resiliently biasing the second shaft.

In some scenarios, the methods may also include: causing at least one flexible tab portion of an inner shank part of the hollow shank to bend out and away from the inner shank part as the external object is being received in the recess; causing a protrusion of the at least one flexible tab portion to snap into a detent of the external object as the external object is being further received in the recess; and/or using an outer shank part of the hollow shank to prevent bending of the at least one flexible tab portion out and away from the inner shank part after the protrusion of the at least one flexible tab portion has snapped into the detent of the external object.

In those or other scenarios, the methods may comprise securing the surgical instrument to the external object after the external object has been received in the recess. The surgical instrument may be secured to the external object by sliding an outer shank part of the hollow shank in the first direction along an elongate length of the inner shank part of the hollow shank until a distal end of the outer shank part covers a portion of a distal end of the inner shank part. The surgical instrument may be released from the external object. The outer shank part is reliantly biased such that the outer shank part slides in the second direction along the elongate length of the inner shank part until the distal end of the outer shank part no longer covers the portion of the distal end of the inner shank part.

The present document also relates to a surgical instrument. The surgical instrument may include: a hollow shank with a distal end having a recess sized and shaped to receive at least a portion of an external object; a first shaft that is rotatably disposed within the hollow shank; and a second shaft that is disposed in the hollow shank so as to be aligned with and in contact with the first shaft. The second shaft: experiences translational movement along a central axis of the surgical instrument in a first direction towards the recess, in response to rotation of the first shaft; and experiences translational movement along the central axis of the surgical instrument in a second direction opposed from the first direction, after traveling into the recess. The translational movement of the second shaft part in each of the first and second directions may be caused by (i) a sliding engagement between ramped surfaces of the first and second shaft parts and/or (ii) a resilient member resiliently biasing the second shaft.

The hollow shank may include an inner shank part and an outer shank part. The inner shank part may have at least one flexible tab portion capable of being bent out and away from the inner shank part as the external object is being received in the recess. A protrusion of the flexible tab portion is capable of snapping into a detent of the external object as the external object is being further received in the recess. The outer shank part may be used to prevent bending of the flexible tab portion out and away from the inner shank part after the protrusion of the flexible tab portion has snapped into the detent of the external object.

In some scenarios, the surgical instrument is secured to the external object after the external object has been received in the recess. The surgical instrument may be secured to the external object by sliding an outer shank part of the hollow shank in the first direction along an elongate length of the inner shank part of the hollow shank until a distal end of the outer shank part covers a portion of a distal end of the inner shank part. The surgical instrument is releasable from the external object. In this regard, the outer shank part is resiliently biased such that the outer shank part is caused to slide in the second direction along the elongate length of the inner shank part until the distal end of the outer shank part no longer covers the portion of the distal end of the inner shank part.

The foregoing and other objects, features and advantages of the invention will be apparent from the following more particular descriptions of exemplary embodiments of the invention as illustrated in the accompanying drawings wherein like reference numbers generally represent like parts of the disclosure.

BRIEF DESCRIPTION OF DRAWINGS

The following drawings are illustrative of particular embodiments of the present disclosure and therefore do not limit the scope of the present disclosure. The drawings are not to scale and are intended for use in conjunction with the explanations in the following detailed description.

FIGS. 3-12 provide a series of illustrations that are useful for understanding how the head locker shown in FIGS. 1-2 operates to couple a receiver to a bone screw.

DETAILED DESCRIPTION

Figure 1:
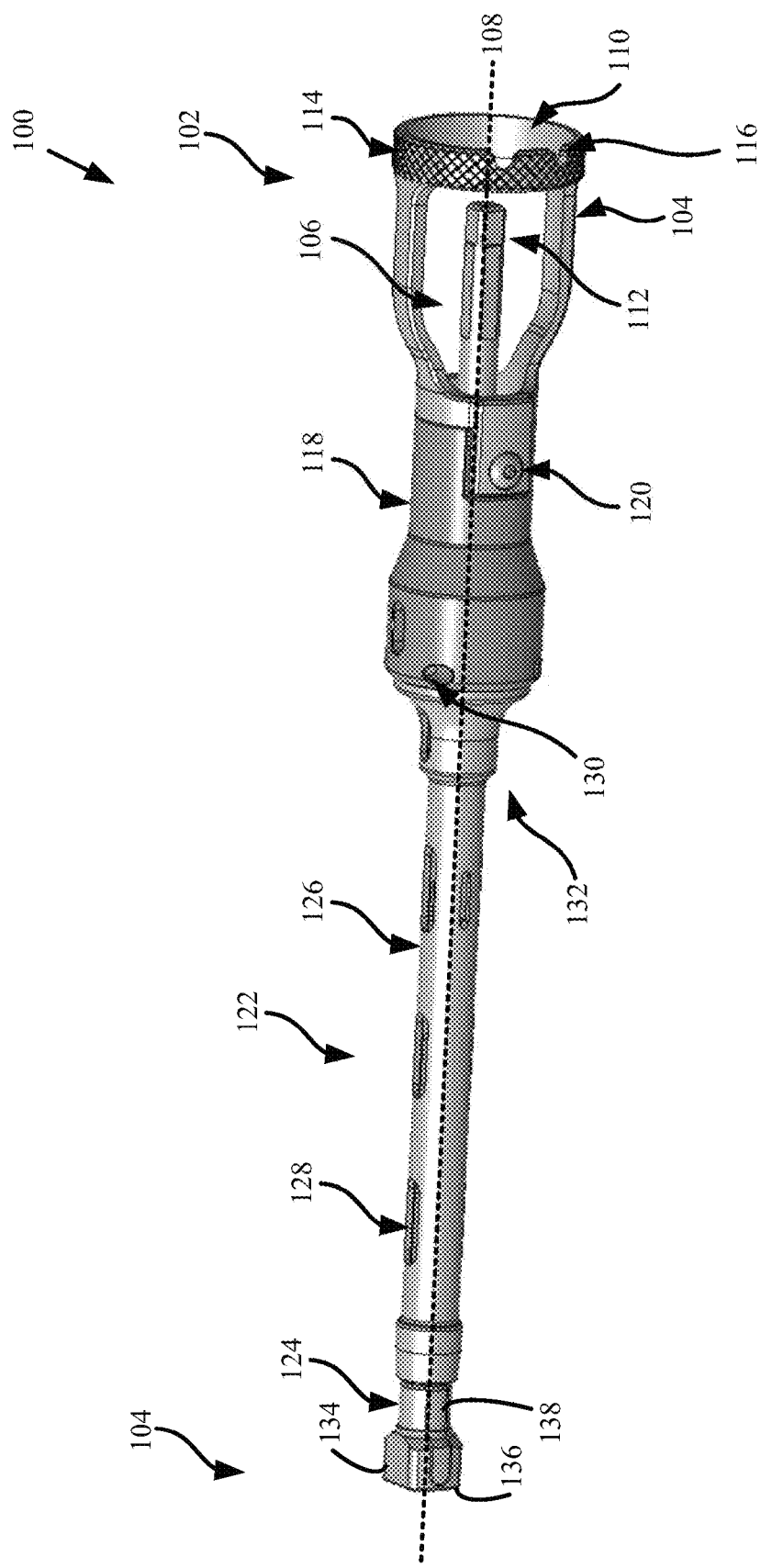
FIG. 1 is a perspective view of an illustrative head locker (or surgical instrument).

The following discussion omits or only briefly describes certain conventional features related to surgical systems for treating the spine, which are apparent to those skilled in the art. It is noted that various embodiments are described in detail with reference to the drawings, in which like reference numerals represent like parts and assemblies throughout the several views. Reference to various embodiments does not limit the scope of the claims appended hereto. Additionally, any examples set forth in this specification are intended to be non-limiting and merely set forth some of the many possible embodiments for the appended claims. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

Embodiments of the present disclosure relate generally, for example, to medical devices and methods for treating musculoskeletal disorders, and more particularly, to surgical systems and methods for treating the spine. Embodiments of the devices, methods, and systems are described below with reference to the Figures.

Figure 2:
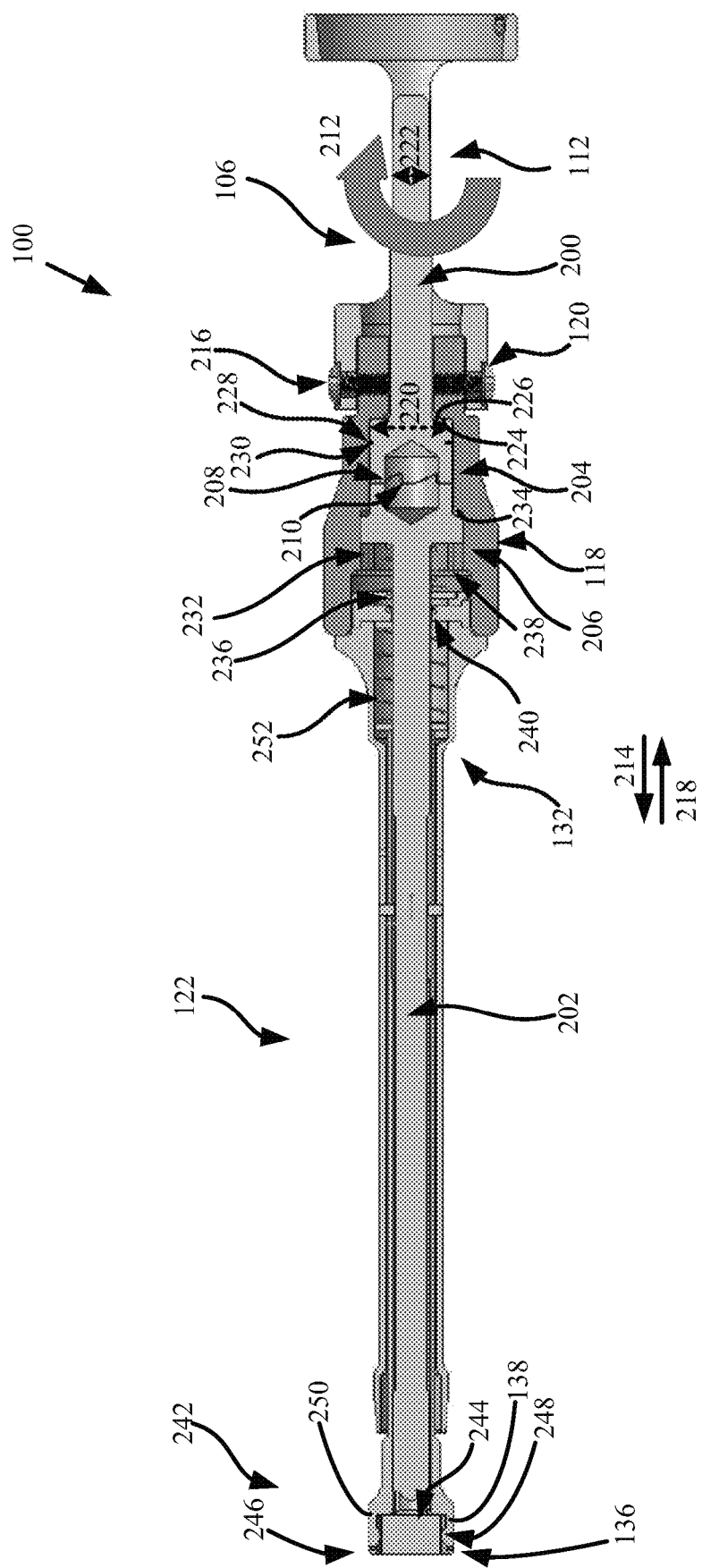
FIG. 2 is another perspective view of the cross sectional view of the head locker shown in FIG. 1.
Figure 5:
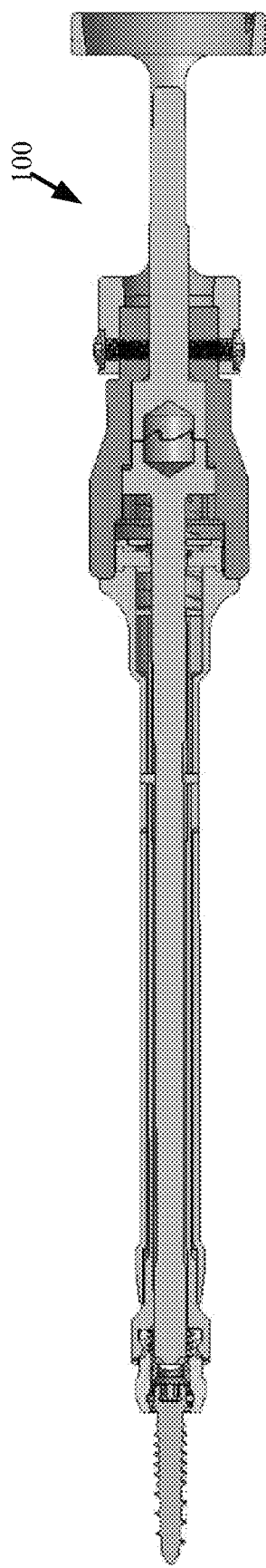
Figure 14:
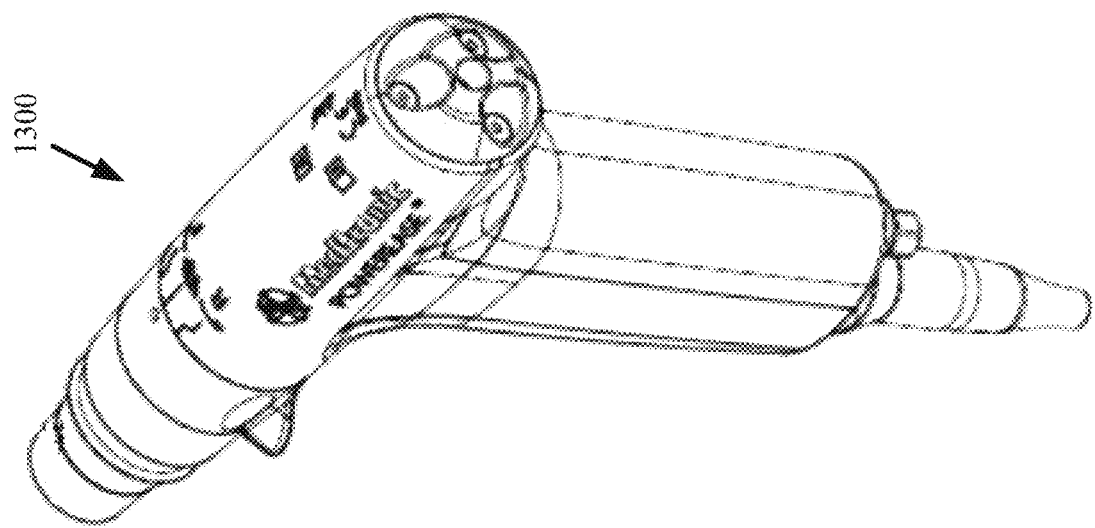
FIGS. 13-14 each provide a person perspective view of an illustrative external power instrument or tool that can be used with the head locker shown in FIGS. 1-13.
Figure 13:
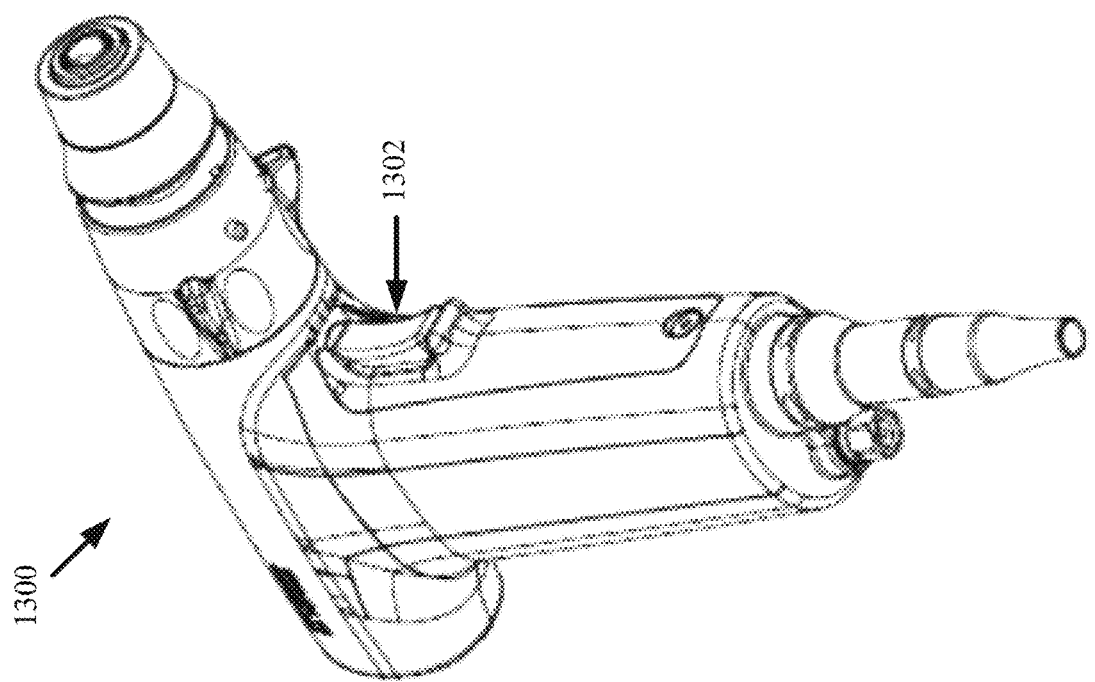

FIG. 1 provides a perspective view of a head locker (or surgical instrument) 100. A cross-sectional view of the head locker 100 is provided in FIG. 2. As shown in FIGS. 1-2, the head locker 100 comprises an enlarged proximal end 102 having a socket 104 for receiving a rotational part of an external instrument or tool. An illustrative external power instrument 1300 is shown in FIGS. 13-14. The external power instrument 1300 can include, but is not limited to, a high-speed surgical drill that has a part number 66320805 and is available from Medtronic of Minneapolis, Minn.

An elongate post 106 is provided within the socket 104 that is aligned with and extends along a central axis 108 of the head locker 100 in a direction towards an opening 110 of the socket 104. A free proximal end 112 of the post 106 is sized and shaped to be received in a socket of the external power instrument's rotational part. The post's free proximal end 112 and external power instrument's rotational part socket are designed such that the external power instrument is able to cause rotation of the post 106 in a clockwise direction and/or a counter clockwise direction. In the scenario shown in FIGS. 1-2, the free proximal end 112 has a square shape. The present solution is not limited in this regard since the free proximal end 112 can have other shapes selected in accordance with a given application (e.g., a cross shape, a star shape or any other shape that allows the transfer of torque to the post 106).

Notably, the socket 110 has a sidewall 114 with one or more notches 116 formed therein. The notches(s) 116 provide(s) a means for the external power instrument 1300 to engage the head locker in such a way that torque can be transferred from the external power instrument to the post 106 of the head locker, but not to the socket sidewall 114 of the head locker. When the external power instrument 1300 is coupled to the proximal end 102 of the head locker 100, the sidewall 114 remains in a constant position relative to the external power instrument 1300. In contrast, the post 106 of the head locker 100 can rotate relative to the external power instrument 1300 when a trigger (e.g., 1302 of FIG. 13) is depressed by a user of the external power instrument.

As shown in FIG. 2, the post 106 comprises two shafts 200, 202. The first shaft 200 comprises the free proximal end 112 that engages the external power instrument 1300 so that torque can be transferred to the post 106 from the external power instrument, as described above. The first shaft 200 also comprises an opposing distal end 204 that abuts and is in contact with a proximal end 206 of the second shaft 202. Distal end 104 of the first shaft 200 and proximal end 206 of the second shaft 202 comprise shaped surfaces 208, 210 which engage each other so that rotation of the first shaft 200 in the clockwise direction 212 (or alternatively in a counter clockwise direction) causes translation of the second shaft 202 in direction 214. In this regard, each shaped surface 208, 210 comprises a plurality of ramps that slide against each other in response to the first shaft's rotation, whereby the translational movement of the second shaft 202 occurs.

A housing 118 is provided for housing the ends 204, 206 of the shafts 200, 202 in a manner that ensures the ends 204, 206 remain aligned with each other and with the central axis 108 of the head locker 100 at all times. The socket 104 is securely coupled to the housing 118 via one or more mechanical couplers 120, 216. The mechanical couplers can include, but are not limited to, screws. Other couplers may alternatively or additionally be employed. These other couplers include, but are not limited to, adhesives and welds.

The first shaft 200 is disposed within the housing 118 such that it can rotate therein in clockwise and/or counter clockwise direction(s), but is unable to move linearly along the central axis 108 in opposing directions 214, 218 therein. In this regard, it should be understood that the first shaft's distal end 204 has a width 220 which is greater than a width 222 of the first shaft's free proximal end 112. In effect, the first shaft's distal end 204 comprises a flange with a surface 224 that engages an inner surface 226 of the housing 118, whereby the first shaft 200 is prevented by the housing from traveling in direction 218 along central axis 108. The first shaft 200 is also prevented from traveling in the opposing direction 214 along central axis 108 by, for example, an inward extending protrusion 228 of the housing 118 that is disposed within a circumferential groove 230 formed in an exterior surface of the first shaft's distal end 204.

The second shaft 202 is disposed within the housing 118 such that it can move linearly in opposing directions 214, 218 therein, but is prevented from rotating relative to the housing 118. In this regard, it should be understood that the proximal end 206 of the second shaft 202 is able to slide within an interior space 232 of the housing 118. Notably, the second shaft's proximal end 206 comprise a flange that (i) may optionally engage a surface 234 of the housing 118 such that the second shaft's movement in direction 218 is limited by the housing in addition to the first shaft 200, and (ii) may optionally engage a surface 238 of the housing 118 such that the second shaft's movement in direction 214 is also limited. The rotational movement of the second shaft 202 can be prevented, for example, by chamfered portions (not shown) of the second shaft's flange, and/or a protrusion (not shown) of the housing disposed in an elongate channel (not shown) formed in the second shaft's flange so as to extend parallel to the central axis 108. The present solution is not limited by the particulars of these examples.

A resilient member 236 is provided that resiliently biases the second shaft 202 towards the first shaft 200. The resilient member 236 provides a means to cause the second shaft 202 to automatically and periodically return to the unengaged position shown in FIG. 2 as the first shaft 200 rotates and ramped surfaces 208, 210 slide against each other. The resilient member 236 can include, but is not limited to, a spring, a coil, a piece of rubber, and/or foam.

The second shaft 202 is movably disposed within a hollow shank 122. The hollow shank 122 is securely coupled to the housing 118 via one or more couplers 130. The coupler(s) can include, but is(are) not limited to, screw(s), adhesive and/or weld. The hollow shank 122 has an enlarged proximal end 132 with a wall 240 structurally supporting the resilient member 236 and preventing the resilient member 236 from being pushed in direction 214 out of the housing 118.

The hollow shank 122 comprises two parts, an inner shank part 124 securely coupled to an outer shank part 126. The outer shank part 126 has one or more through holes 128 formed therein to facilitate cleaning of the inner shank part 124.

The inner shank part 124 has a distal end 242 with a recess 244 size and shaped to receive a portion of an external object (e.g., a receiver 300 of FIGS. 3-12) during a medical procedure (e.g., the placement of an implant in a patient). The sidewalls 134, 136, 246 of the recess 244 are formed of a rigid material, such as metal. At least two of the sidewalls 136, 246 have flexible tab portions 138, 250 that are able to bend in and out of the inner shank part's distal end 242. In some scenarios, the flexible tab portions 138, 250 are formed of the same material as the remaining portions of the sidewalls 136, 250, but with smaller thicknesses as compared thereto. Each of the flexible tab portions 138, 250 has a protrusion 248 (e.g., a convex dimple) size and shaped to be received in a detent (e.g., detent 302, 314 of FIG. 3) of the external object (e.g., receiver 300 of FIG. 3). The protrusions 248 and detents provide a way to couple the inner shank part 124 to the external object.

The outer shank part 126 is provided to prevent the protrusions 248 from dislodging from the detents during use of the head locker 100. Accordingly, the outer shank part 126 provides a movable sleeve for the inner shank part 124. The outer shank part 126 can be manually moved in direction 214 when the protrusions 248 of the inner shank part 124 are disposed in the detents of the external object. The outer shank part 126 can be locked in positon via a mechanical lock mechanism (not shown in FIGS. 1-2) once it reaches an engaged position (e.g., shown in FIG. 5). Mechanical lock mechanisms are well known in the art, and therefore will not be described herein. The mechanical lock mechanism can include, but is not limited to, a latch, and/or a depressible button disposed on the inner shank part 124 which extends through a through hole of the outer shank part 126 when aligned therewith. In the locked position, bending of the flexible tab portions 138, 250 out of the sidewalls 136, 246 is prevented by the outer shank part 126.

Notably, the outer shank part 126 is resiliently biased by a resilient member 252. Resilient member 252 provides a means to cause the outer shank part 126 to automatically return from a locked position (e.g., the position shown in FIG. 5) to the unlocked position shown in FIG. 2 when the mechanical lock mechanism is unlocked. The resilient member 252 can include, but is not limited to, a spring, a coil, a piece of rubber, and/or foam.

In some scenarios, all of the components comprising the head locker 100 are formed of the same material, such as metal. In other scenarios, at least the housing 118 is formed of a material (e.g., plastic or rubber) that is different than the material (e.g., metal) that the other components of the head locker are formed of.

FIGS. 3-11 provide illustrations that are useful for understanding operations of the head locker 100 in a medical procedure scenario. In FIGS. 3-11, the head locker 100 is being used to securely couple a receiver 300 to a screw 304 (e.g., a bone screw). Notably, a crown 308 is disposed within the receiver 300 prior to the receiver 300 being disposed on the head 310 of the screw 304. Screws, receivers and crowns are well known in the art, and therefore will not be described herein.

As shown by FIG. 3, the process begins with the head locker 100 being placed in proximity to the receiver 300. The central axis 108 of the head locker 100 is aligned with the central axis 306 of the receiver 300 and screw 304. Once aligned, the head locker 100 is manually moved in direction 312 towards the receiver 300. As a result of this movement, sidewalls 400, 402 of the receiver 300 are received into the recess 244 of the head locker's inner shank part 124. The receiver sidewalls 400, 402 slidingly engage inner surfaces of the hollow shank's flexible tab portions 138, 250. This sliding engagement causes the flexible tab portions 138, 250 to be respectively pushed in directions 404, 406 out and away from the head locker's inner shank part 124. Once aligned, protrusions 248 of the flexible tab portions 138, 250 will slide into detents 302, 314, as shown in FIG. 4.

At this time, the outer shank part 126 is manually moved in direction 312. This linear movement of the outer shank part 126 causes the outer shank part to be transitioned from an unlocked position shown in FIGS. 3-4 to a locked position shown in FIGS. 5-6. In the locked position, the outer shank part 126 prevents bending of the flexible tab portions 138, 250 in directions 404, 406, whereby the inner shank part 124 is securely coupled to the receiver 300.

Figure 6:
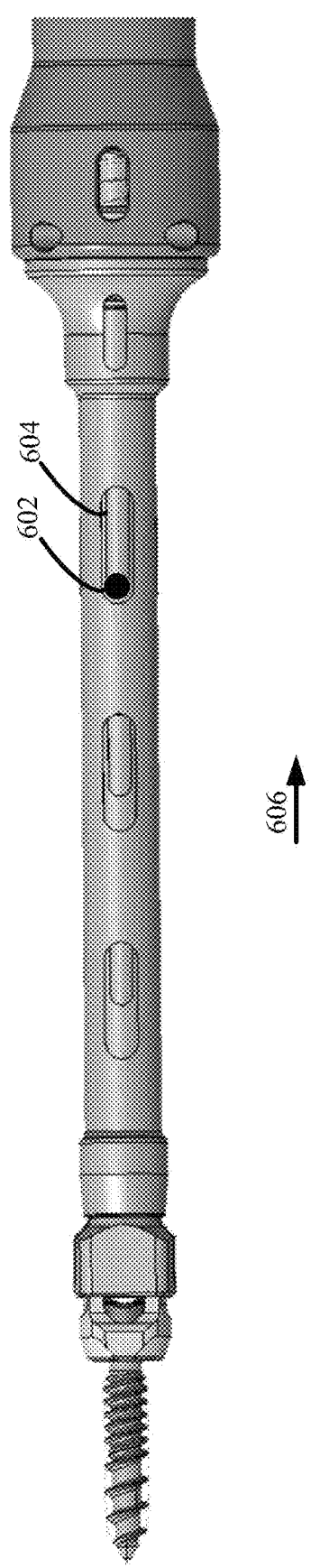

A lock mechanism is provided to retain the outer shank part in the locked position. The lock mechanism can include, but is not limited to, a resiliently biased post 602 that is pushed into an aperture 604 formed in the outer shank part when the post becomes aligned with the aperture 604. The post 602 prevents the outer shank part from moving in direction 606. The aperture 604 can include (i) a cleaning hole 128 as shown in FIG. 6 or (ii) alternatively could include another through hole formed in the outer shank part. In scenario (i), the aperture/hole has a dual purpose of (a) facilitating cleaning of the inner shank part and (b) facilitating locking/unlocking of the outer shank part to/from the inner shank part.

Subsequently, an external instrument (e.g., drill 1300 of FIGS. 13-14) is coupled to socket 104 provided at the proximal end 102 of the head locker 100, as shown in FIG. 6. The external instrument can include, but is not limited to, the high-speed surgical drill 1300 shown in FIGS. 13-14. A trigger (e.g., trigger 1302 of FIG. 13) of the external instrument is actuated so that torque is transferred from the external instrument to the elongate post 106 of shaft 200 that is provided within the head locker's socket 104.

This torque causes the shaft 200 to rotate relative to the socket's sidewall 114 and the housing 118. Consequently, a ramped surface 208 of the shaft 200 slides against a ramped surface 210 of shaft 202 as shown in FIGS. 7-8. This sliding engagement between shafts 200, 202 causes translational movement of shaft 202 in direction 800 along the head locker's central axis 108, as shown in FIG. 8. As a result of this translation movement, the distal end 802 of shaft 202 comes in contact with crown 308 (as also shown in FIG. 8) and applies a pushing force on crown 308 (as shown in FIG. 9).

The pushing force causes the crown 308 to move in direction 800 towards the screw 304. In turn, the crown 308 applies a pushing force on a first ring 900. In effect, the first ring 900 is pushed by the crown 308 in direction 800 until the first ring 900 moves into a first groove 904 formed on an inner surface of the receiver 300. Notably, the first ring 900 prevents a second ring 902 from moving into a second groove 906 formed on an inner surface of the receiver 300. When this occurs, the receiver 300 is securely coupled to the screw 304.

Thereafter, rotation of the shaft 200 continues until the ramp surface slides a certain amount which allows a resilient member 236 to resiliently bias and return the shaft 202 back to its unengaged position shown in FIG. 10. Notably, in the unengaged position, there is no gap between ramped surfaces 208, 210 as shown in FIG. 10. In contrast, in the engaged position, a gap 908 exists between a portion of the ramped surfaces 208, 210 as shown in FIG. 9. In the unengaged position, shaft 202 is no longer in contact with the crown 308.

Next as shown FIG. 11, the lock mechanism 602 is depressed such that the resilient member 252 is able to resiliently bias the outer shank part 126 in direction 606. The resilient biasing causing the outer shank part 126 to transition from its locked position shown in FIG. 10 to its unlocked position shown in FIG. 11. In the unlocked position, the flexible tab portions 138, 250 are able to once again bend out and away from the head locker's inner shank part 124. As such, when a pulling force is applied to the head locker 100 in direction 606, the flexible tab portions 138, 250 slide out of detent 302, 314 of the receiver 300, whereby the head locker's inner shank part 124 is decoupled from the receiver 300. The head locker 100 is then moved out and away from the receiver 300, as shown in FIG. 12.

As evident from the above-discussion, the head locker 100 provides a means for quickly locking a head (e.g., a receiver and/or crown) to a screw. This can be done with the same instrument that is used to insert the head (e.g., the receiver is coupled to the instrument prior to being placed on the screw's head). If the heads are inserted by different means, the need to quickly attach to each head, and then lock the heads becomes more important. This instrument allows a user to push don with the instrument on the head that is already disposed on the screw. This pressure causes the instrument to securely attach to the head. Then, the user can pull a power tool's trigger to spin an upper shaft part of the instrument. This causes ramped surface of the two shaft parts to slidingly engage each other, whereby a translation of a lower shaft part occurs. The lower shaft part's translational movement causes a pushing force to be applied to the crown for locking the head on the screw. To release the instrument from the head, the user only has to lift the instrument up.

Figure 15:
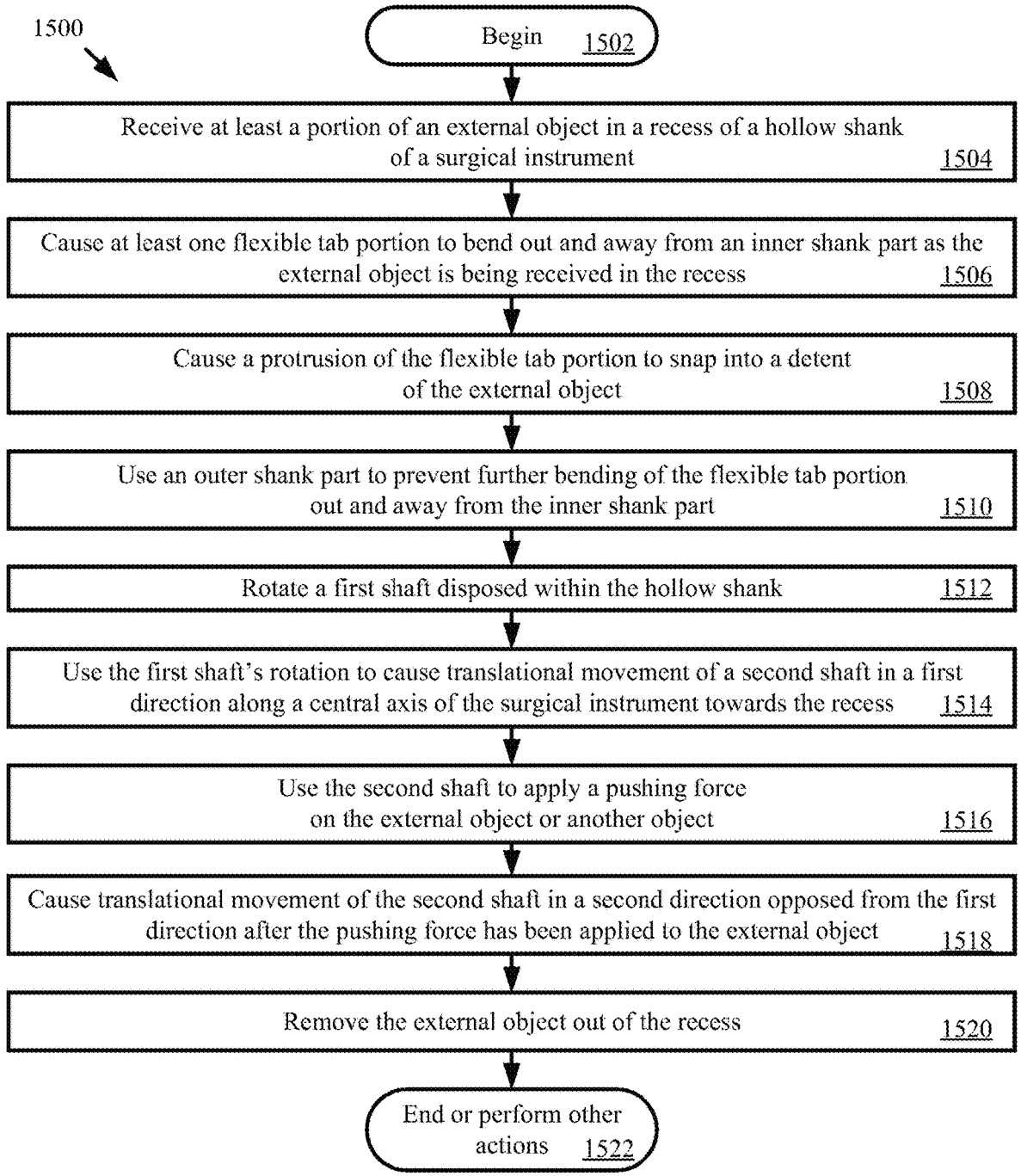
FIG. 15 provides a flow diagram of an illustrative method for coupling a receiver to a bone screw (e.g., during a medical procedure).

Referring now to FIG. 15, there is provided a flow diagram of an illustrative method 1500 for operating a surgical instrument (e.g., head locker 100 of FIGS. 1-11). Method 1500 begins with 1502 and continues with 1504 where at least a portion of an external object (e.g., receiver 300 of FIGS. 3-11) is received in a recess (e.g., recess 244 of FIG. 2) of a hollow shank (e.g., hollow shank 122 of FIG. 1). In 1506, at least one flexible tab portion (e.g., flexible tab portion 138, 250 of FIGS. 1-2) of an inner shank part (e.g., inner shank part 124 of FIGS. 1-2) of the hollow shank is caused to bend out and away from the inner shank part as the external object is being received in the recess. This bending is caused by the sliding engagement of the inner shank part and the external object. In 1508, a protrusion (e.g., protrusions 248 of FIG. 2) of the flexible tab portion is caused to snap into a detent (e.g., detent 302, 314) of the external object as the external object is being further received in the recess.

In 1510, an outer shank part (e.g., outer shank part 126 of FIG. 1) of the hollow shank is used to prevent bending of the flexible tab portion(s) out and away from the inner shank part after the protrusion(s) of the flexible tab portion(s) has(have) snapped into the detent(s) of the external object. For example, the outer shank part is slid in the first direction along an elongate length of the inner shank part of the hollow shank until a distal end of the outer shank part covers a portion of a distal end of the inner shank part.

A first shaft (e.g., shaft 200 of FIG. 2) is rotated (e.g., using an external tool 1300 of FIGS. 13-14) in 1512. The first shaft's rotation is used in 1514 to cause translational movement of a second shaft (e.g., shaft 202 of FIG. 2) in a first direction along a central axis (e.g., axis 108 of FIG. 1) of the surgical instrument towards the recess. The second shaft is used in 1516 to apply a pushing force on the external object or another object (e.g., crown 308 of FIG. 3).

In 1518, translation movement of the second shaft in a second direction opposed from the first direction is caused after the pushing force has been applied to the external object. The translational movement of the second shaft part in the first and second directions is caused by (i) a sliding engagement between ramped surfaces of the first and second shaft parts, and/or (ii) a resilient member resiliently biasing the second shaft.

Next, the external object is removed from the recess as shown by 1520. 1520 can involve: releasing a lock mechanism; resiliently biasing the outer shank part such that the outer shank part slides in the second direction along the elongate length of the inner shank part until the distal end of the outer shank part no longer covers the portion of the distal end of the inner shank part; and lifting or otherwise moving the surgical instrument away from the external object. Subsequently, 1522 is performed where method 1500 ends or other actions are performed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method for operating a surgical instrument, comprising:
  receiving at least a portion of an external object in a recess of a hollow shank;
  causing at least one flexible tab portion of an inner shank part of the hollow shank to bend out and away from the inner shank part as the external object is being received in the recess;
  rotating a first shaft disposed within the hollow shank;

using rotation of the first shaft to cause translational movement of a second shaft along a central axis of the surgical instrument in a first direction towards the recess;

applying a pushing force on the external object using the second shaft that is experiencing the translational movement; and causing translational movement of the second shaft in a second direction opposed from the first direction after the pushing force has been applied to the external object.

2. The method according to claim 1, further comprising causing a protrusion of the at least one flexible tab portion to snap into a detent of the external object as the external object is being further received in the recess.

3. The method according to claim 2, further comprising using an outer shank part of the hollow shank to prevent bending of the at least one flexible tab portion out and away from the inner shank part after the protrusion of the at least one flexible tab portion has snapped into the detent of the external object.

4. The method according to claim 1, further comprising securing the surgical instrument to the external object after the external object has been received in the recess.

5. The method according to claim 1, wherein the translational movement of the second shaft part in the first and second directions is caused by a sliding engagement between ramped surfaces of the first and second shaft parts.

6. The method according to claim 5, wherein the translation movement of the second shaft in the second direction is caused further by a resilient member resiliently biasing the second shaft.

7. A method for operating a surgical instrument, comprising:

receiving at least a portion of an external object in a recess of a hollow shank;

securing the surgical instrument to the external object after the external object has been received in the recess;

rotating a first shaft disposed within the hollow shank;

using rotation of the first shaft to cause translational movement of a second shaft along a central axis of the surgical instrument in a first direction towards the recess;

applying a pushing force on the external object using the second shaft that is experiencing the translational movement; and causing translational movement of the second shaft in a second direction opposed from the first direction after the pushing force has been applied to the external object;

wherein the surgical instrument is secured to the external object by sliding an outer shank part of the hollow shank in the first direction along an elongate length of the inner shank part of the hollow shank until a distal end of the outer shank part covers a portion of a distal end of the inner shank part.

8. The method according to claim 7, further comprising releasing the surgical instrument from the external object.

9. The method according to claim 8, further comprising resiliently biasing the outer shank part such that the outer shank part slides in the second direction along the elongate length of the inner shank part until the distal end of the outer shank part no longer covers the portion of the distal end of the inner shank part.

10. A surgical instrument, comprising:

a hollow shank with a distal end having a recess sized and shaped to receive at least a portion of an external object;

a first shaft that is rotatably disposed within the hollow shank; and a second shaft that is disposed in the hollow shank so as to be aligned with and in contact with the first shaft, where the second shaft is adapted to:

experience translational movement along a central axis of the surgical instrument in a first direction towards the recess, in response to rotation of the first shaft; and experience translational movement along the central axis of the surgical instrument in a second direction opposed from the first direction, after traveling into the recess;

wherein the hollow shank comprises an inner shank part and an outer shank part, the inner shank part having at least one flexible tab portion that is configured to bend out and away from the inner shank part as the external object is being received in the recess.

11. The surgical instrument according to claim 10, wherein a protrusion of the at least one flexible tab portion is capable of snapping into a detent of the external object as the external object is being further received in the recess.

12. The surgical instrument according to claim 11, wherein the outer shank part is used to prevent bending of the at least one flexible tab portion out and away from the inner shank part after the protrusion of the at least one flexible tab portion has snapped into the detent of the external object.

13. The surgical instrument according to claim 10, wherein the surgical instrument is secured to the external object positioned in the recess.

14. The surgical instrument according to claim 13, wherein an outer shank part of the hollow shank is adapted to slide in the first direction along an elongate length of the inner shank part of the hollow shank such that a distal end of the outer shank part covers a portion of a distal end of the inner shank part thereby facilitating a securement of the surgical instrument to the external object.

15. The surgical instrument according to claim 14, wherein the surgical instrument is releasable from the external object.

16. The surgical instrument according to claim 15, wherein the outer shank part is resiliently biased such that the outer shank part is adapted to slide in the second direction along the elongate length of the inner shank part until the distal end of the outer shank part no longer covers the portion of the distal end of the inner shank part.

17. The surgical instrument according to claim 10, wherein said ramped surfaces of the first and second shaft parts are slidably engaged.

18. The surgical instrument according to claim 17, wherein a resilient member resiliently biases the second shaft enabling the translation movement of the second shaft in the second direction.

* * * * *